United States Patent [19]

Kramm

[11] Patent Number: 5,766,225
[45] Date of Patent: Jun. 16, 1998

[54] SYSTEM AND METHOD FOR DISTINGUISHING BETWEEN VF/VT BRADYCARDIA OR ASYSTOLE

[75] Inventor: Berthold Kramm, Cadier En Keer, Netherlands

[73] Assignee: Medtronic, Inc., Minneapolis, Minn.

[21] Appl. No.: 673,444

[22] Filed: Jun. 28, 1996

[51] Int. Cl.$^6$ .................................................. A61N 1/39
[52] U.S. Cl. .................................................. 607/4; 128/705
[58] Field of Search .......................... 607/4, 5; 128/702, 128/705

[56] References Cited

U.S. PATENT DOCUMENTS

| | | | |
|---|---|---|---|
| 4,114,628 | 9/1978 | Rizk . | |
| 4,932,407 | 6/1990 | Williams . | |
| 4,953,551 | 9/1990 | Mehra et al. . | |
| 5,163,427 | 11/1992 | Keimel . | |
| 5,174,288 | 12/1992 | Bardy et al. . | |
| 5,188,105 | 2/1993 | Keimel . | |
| 5,193,536 | 3/1993 | Mehra | 607/4 |
| 5,261,400 | 11/1993 | Bardy | 607/5 |
| 5,320,643 | 6/1994 | Roline et al. | 607/28 |
| 5,350,401 | 9/1994 | Levine | 607/4 |
| 5,458,619 | 10/1995 | Olson | 607/4 |

OTHER PUBLICATIONS

US Application 08/622802, L. Wang, "Verification of Capture by Sensing Evoked Response Across Cardioversion Electrotes" filed Mar. 27, 1996.

*Primary Examiner*—William E. Kamm
*Assistant Examiner*—George R. Evanisko
*Attorney, Agent, or Firm*—Michael J. Jaro; Harold Patton

[57] ABSTRACT

A system and method for more reliably detecting and treating arrhythmias such as ventricular fibrillation and tachycardia are provided. The system reacts to the detection of VF/VT by first looking for one or more sensed R waves to confirm arrhythmia. If the arrhythmia is confirmed, an appropriate shock is delivered directly. However, if the arrhythmia is not confirmed following a timed out confirmation duration, a pace pulse is delivered, following which the system looks to see if the pace pulse has resulted in capture of the patient's ventricle. Capture is determined by a examining sensed far field signals that correlate with the delivered pace pulse. In a preferred embodiment, the far field signals are sensed between a ventricular fibrillation coil and a second electrode, the second electrode suitably being either an SCV electrode or the surface of the implanted defibrillator unit. If capture is determined, delivery of a shock is aborted, and the patient may be further treated with pacing therapy. If capture is not found, this indicates that the arrhythmia remains, even though not sensed during the confirmation duration, and shock therapy is applied directly.

20 Claims, 4 Drawing Sheets

SYSTEM AND METHOD FOR DISTINGUISHING BETWEEN VF/VT BRADYCARDIA OR ASYSTOLE

BACKGROUND OF THE INVENTION

This invention relates to a system and method for defibrillation and/or cardioversion and, more particularly, for safely determining whether or not a detected arrhythmia has been sustained, and for avoiding delivering of an inappropriate shock when in fact arrhythmia has not been sustained and the patient has marked bradycardia or asystole.

The implantable cardioverter defibrillator (ICD) device has been shown to be effective in terminating episodes of ventricular fibrillation (VF) and ventricular tachycardia (VT). This capacity for detecting and terminating potentially lethal arrhythmias such as VF/VT has been further combined with the pacemaker function, the combined unit being referred to as a PCD (pacemaker/cardioverter/defibrillator) type device, such as made by Medtronic, Inc., the assignee of this invention. The capability of this device has been further enhanced by the development of leads for providing transvenous ventricular defibrillation. See, for example, U.S. Pat. Nos. 4,932,407 and 5,174,288, disclosing lead systems providing transvenous ventricular defibrillation and cardioversion electrodes. Likewise, subcutaneous defibrillation leads may be used. The PCD or ICD type device, together with the improved leads, make it possible to provide relatively efficient systems for terminating VT or VF.

A remaining problem with such systems for dealing with such dangerous arrhythmias is the potential for delivering an inappropriate shock. In particular, this invention addresses the problem where an arrhythmia such as VT or VF has been accurately sensed but has not been sustained. In such a situation, the detection of VT or VF results in the system being primed to deliver a shock. If, however, the patient exhibits either marked bradycardia or asystole when the device seeks confirmation of the previously detected arrhythmia, the lack of a sensed signal can be taken as confirmation of an underlying arrhythmia, resulting in an inappropriate shock. The total number of inappropriate shocks varies according to the literature, but remains significant enough to be regarded as a major challenge. In order to deal with this, ICD and PCD type devices have incorporated a variety of reconfirmation algorithms, which are aimed at confirming the underlying arrhythmia after it has been detected, thereby reducing the number of inappropriate shocks. Of course, the confirmation, or reconfirmation algorithm must take into account that failure to deliver a shock when a potentially lethal arrhythmia persists cannot be accepted; the arrhythmia confirmation needs to be substantially 100 percent.

As an example of the above, in a typical PCD type device, there is a confirmation period following detection of, for example, a condition of fibrillation. This confirmation period serves two purposes. First, an attempt is made to deliver shock therapy synchronously with a patient heartbeat, when a sustained arrhythmia is sensed. For this reason, the system may look for one or two R waves that are consistent with the arrhythmia, and deliver a synchronous shock. However, if a predetermined confirmation period expires without any sensed signal, then a shock is delivered asynchronously at the end of such period. This could likely be the correct result, where the absence of a sensed R wave is reflective of an underlying fibrillation or other arrhythmia. However, the time out of the confirmation period can also result from the patient having reverted to marked bradycardia or asystole after a non-sustained arrhythmia. It is clear that it is desirable to distinguish such a marked bradycardia or asystole, i.e., a non-sustained arrhythmia, from an undersensed real arrhythmia (VF/VT). The safe differentiation between a bradycardia episode and a VF/VT episode is desirable in order to provide delivery of a more appropriate pacing therapy instead of an inappropriate shock.

There thus is presented a significant need for improving the confirmation routine of a PCD or ICD type device, so as to avoid shock delivery during the confirmation period in the event of a bradycardia condition (e.g., bradycardia or asystole) after a non-sustained arrhythmia, without sacrificing the sensitivity of arrhythmia detection and following therapy. It is also important, in either case, to deliver the most appropriate and most beneficial therapy without delay: in the case of bradycardia or asystole after a non-sustained arrhythmia, this is appropriate anti-bradycardia pacing, while in the case of the ventricular arrhythmia this constitutes prompt defibrillation or cardioversion therapy.

SUMMARY OF THE INVENTION

In accordance with the above need in the art, there is provided a system and method for detecting cardiac arrhythmias such as ventricular fibrillation or tachycardia, the system having the capability following such a detection for accurately distinguishing between a sustained arrhythmia requiring shock therapy and a non-sustained arrhythmia which is replaced by brady conditions of the sort for which only pacing therapy is desired. The system includes a PCD type unit and a suitable electrode system such as an endocardial lead with defib and pacing electrodes. The system continually senses cardiac signals and detects from such sensed signals an occurrence of VT/VF. Following this, the system enters a confirmation sequence where it seeks to deliver a shock in the event that sustained VF or VT is confirmed. The confirmation sequence lasts for at least a predetermined brady interval, and if arrhythmia is not positively confirmed, or a normal sinus rhythm is not detected, a pace pulse is delivered at the time out of the confirmation interval. The system looks to determine whether the delivered pace pulse has captured the heart, preferably by examining any signal sensed at the defibrillation far field electrodes, which sensed signal is indicative of heart capture. If capture is sensed within a predetermined interval following the pace pulse, then the system continues in a pacer mode, e.g., VVI pacing. However, if capture is not sensed, this verifies that the underlying arrhythmia has been sustained and a shock is delivered at the time out of the predetermined interval following delivery of the pace pulse. The capture detection feature is "fail-safe" with respect to reacting to a dangerous therapy, since failure to detect capture results in delivery of a shock.

DETAILED DESCRIPTION OF THE PREFERRED EMBODIMENTS

Figure 1:
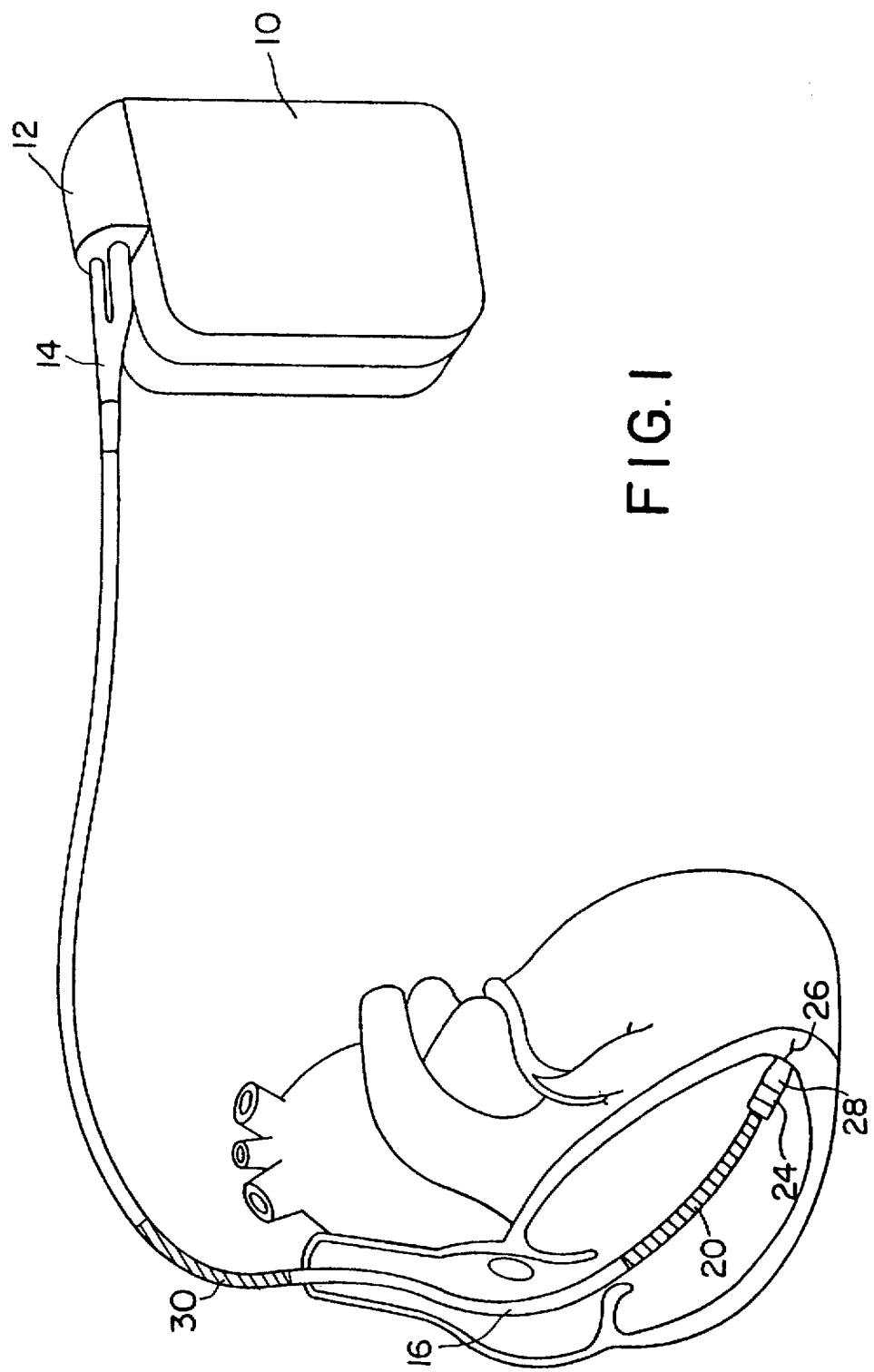
FIG. 1 is an illustration of a PCD type system according to the present invention.

Referring now to FIG. 1, there are illustrated a defibrillator 10 and a lead 16, making up the PCD type system of this invention. The lead shown is illustrative, it being noted that other specific forms of leads are within the scope of this invention. See, for example, the above-referenced U.S. Pat. Nos. 4,932,407 and 5,174,288, as well as 5,261,400, all of which are incorporated by reference. The lead as illustrated has, located adjacent the distal end, an extendable helix electrode 26 and a ring electrode 24, the helix electrode being mounted retractably within an insulative head 28. Electrodes 24 and 26 are utilized for bipolar cardiac pacing and for sensing ventricular depolarizations. While electrodes 24, 26 may be used for bipolar pacing and sensing, electrode 26 may be used in conjunction with a surface of device can 10, which surface acts as a common or indifferent electrode in what is termed unipolar operation. The lead also carries a coil electrode 20, sometimes referred to as the RV coil, for delivering defibrillation and/or cardioversion pulses. Electrode 20 is positioned on the lead so that when the distal tip is at the apex of the ventricle, coil 20 is positioned in the right ventricle. Lead 16 may also carry, optionally, an SCV coil 30, positioned in the subclavian vein, which can be used for R wave sensing and/or applying cardioversion pulses. Lead 16 carries respective concentric coil conductors, separated from one another by appropriate means such as tubular insulative sheaths and running the length of the lead for making electrical connection between the PCD device 10 and respective ones of electrodes 20, 24, 26 and 30.

An implantable PCD type device, or defibrillator 10, is shown in combination with the lead, with the lead connector assembly 14 being inserted into the connector block 12 of the device 10. A specific example of a defibrillation pulse generator which may be used in conjunction with the present lead, is disclosed in U.S. Pat. No. 4,953,551. Other PCD type units can be used; reference is made to U.S. Pat. Nos. 5,163,427 and 5,188,105 as disclosing illustrative forms of apparatus for delivering cardioversion and defibrillation pulses. As used herein, the term "PCD type" device refers to any device which can apply both pacing therapy and shock therapy for controlling arrhythmias.

Figure 2A:
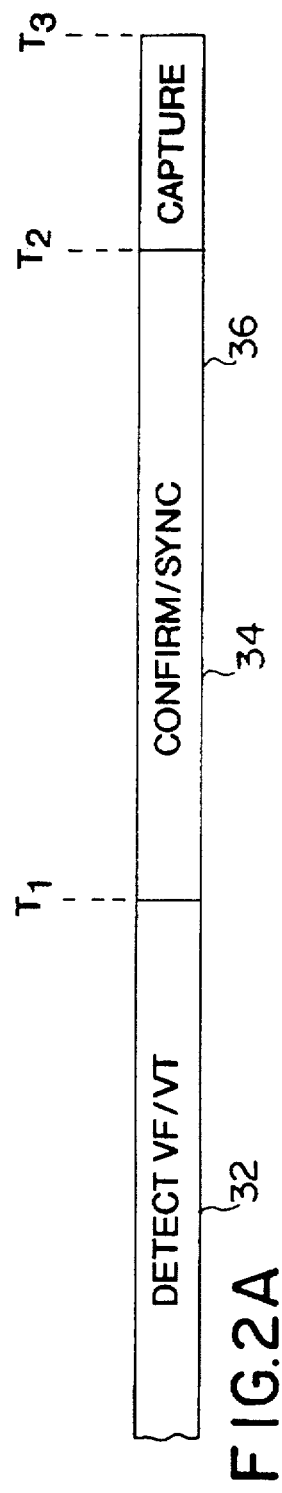
FIG. 2A is a simple timing diagram illustrating the operation of a PCD type device embodying the present invention.

Referring now to FIG. 2A, there is shown a simple timing diagram, which illustrates the timing sequence and the primary operations of the present invention. As shown at 32, the PCD type unit is in a detect mode, and makes a finding of an arrhythmia (VF/VT) following a charging period. Following this at $T_1$, the system sets up a confirm/sync interval 34, which is shown as being of predetermined duration, but which may in fact be of variable duration, as discussed further below. During the confirm/sync duration 34, the system seeks either to confirm the arrhythmia and to deliver a synchronized shock; or time out the interval without confirmation. In this simple illustration, looking for a normal sinus rhythm is not shown. The confirm/sync interval, illustrated as $T_2-T_1$ has a duration corresponding to a predetermined brady escape interval, e.g., corresponding to a pacing rate in the range of 60–120 bpm. When the confirm/sync escape interval runs out at $T_2$, a ventricular pace pulse is delivered (instead of a shock). A capture interval is established, illustrated at 36, having a duration of about 200 ms and terminating at time $T_3$. During this interval the system monitors a far field signal, such as between electrode 20 and the can 10, or between electrode 20 and SCV coil 30. If there is a signal sensed between these far field electrodes, and the signal correlates to the ventricular pacing stimulus, this indicates ventricular capture and is clear evidence of a bradycardia or asystole. This conclusion follows because only in such a circumstance is there enough myocardial mass stimulated so as to produce a signal which can be detected as a far field signal, i.e., at electrodes displaced from the site where the pace pulse is delivered. Following capture, the system suitably maintains a pacing mode. Conversely, if there is no correlation between the ventricular pacing stimulus and the far field signal during the capture duration, this is a certain indication of the presence of an undersensed ventricular arrhythmia. It is noted that in the case of VF/VT, the myocardial mass which can be stimulated is too small to produce a detectable far field signal, i.e., far field IECG. Under these circumstances, a shock of appropriate power, depending upon the nature of the arrhythmia is delivered at time $T_3$.

Figure 2B:
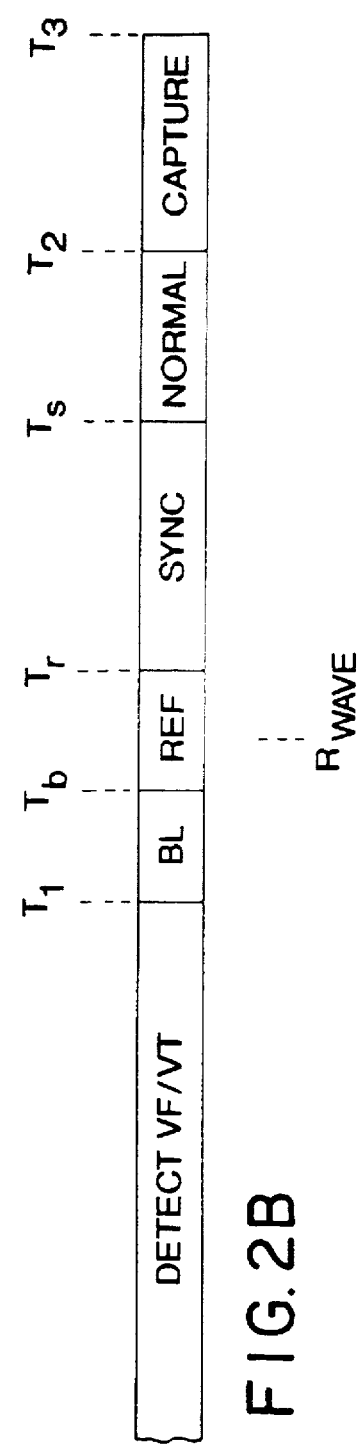
FIGS. 2B and 2C are timing diagrams illustrating specific arrangements of the confirmation period and follow-up capture period in accordance with this invention.

Referring now to FIG. 2B, there is shown a timing diagram of a more specific illustrative embodiment. As was the case in FIG. 2A, fibrillation (or other ventricular arrhythmia) is detected at time $T_1$. The confirm/sync duration, $T_2-T_1$, is structured to include plural intervals, namely a blanking interval (Bl) which extends to a time $T_b$; a refractory interval (Ref) which extends through to time $T_r$; a sync interval which follows $T_r$ and extends to time $T_s$; and a "normal" interval which extends from $T_s$ until $T_2$. As presented, the timing diagram is illustrative, and the respective durations are not necessarily drawn to scale. The entire duration from $T_1$ to $T_2$ constitutes a brady interval corresponding to a rate in the range of about 60–120 bpm. Any R wave which is sensed during the blanking duration is ignored. An R wave sensed during the refractory interval may be utilized or not, depending upon the algorithm chosen. Assuming that an R wave sensed before $T_r$ is not used, the system then looks for the presence of an R wave during the sync interval. An R wave that is sensed during this sync period has come sufficiently rapidly that it is confirmed as an arrhythmia, and a shock is delivered in sync with such sensed R wave. However, an R wave received after $T_s$ but before $T_2$ is deemed to be a normal beat and not to be an arrhythmia, and no shock is delivered; since such a sensed R wave is an indication of a normal heartbeat, or a non-sustained arrhythmia, the arrhythmia is not confirmed, and the episode is terminated. However, if no R wave has been detected by time $T_2$, then a pace pulse is delivered at time $T_2$. The pace pulse is suitably at maximum available pacing output, to optimize the probability of capture. For a standard PCD manufactured by Medtronic, Inc., this is an 8.4 volt pulse at 1.6 ms pulse width. Following delivery of a pace pulse at $T_2$, the system waits until time $T_3$; it then either confirms capture, in which case the system reverts to a pacemaker mode of operation, or in the event of non-capture, delivers appropriate shock therapy.

Figure 2C:
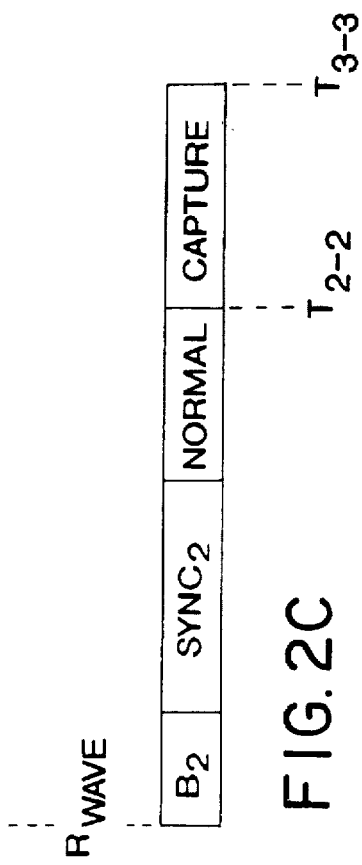

Referring now to FIG. 2C, there is shown another timing diagram, illustrated in relation to the timing of FIG. 2B, to illustrate another exemplary embodiment where a first R wave is sensed during the refractory interval. In this embodiment, the first sensed R wave causes the establishment of a second confirm/sync interval. The difference in this embodiment is that an R wave detected during the first refractory interval causes a second confirm/sync interval to be timed out, but without a refractory interval. This enables syncing on a second R wave if one is found within the second established interval. Failure to confirm results in delivery of a pace pulse at time $T_{2-2}$, and delivery of a shock at time $T_{3-3}$ if the pace pulse does not result in capture.

Figure 3:
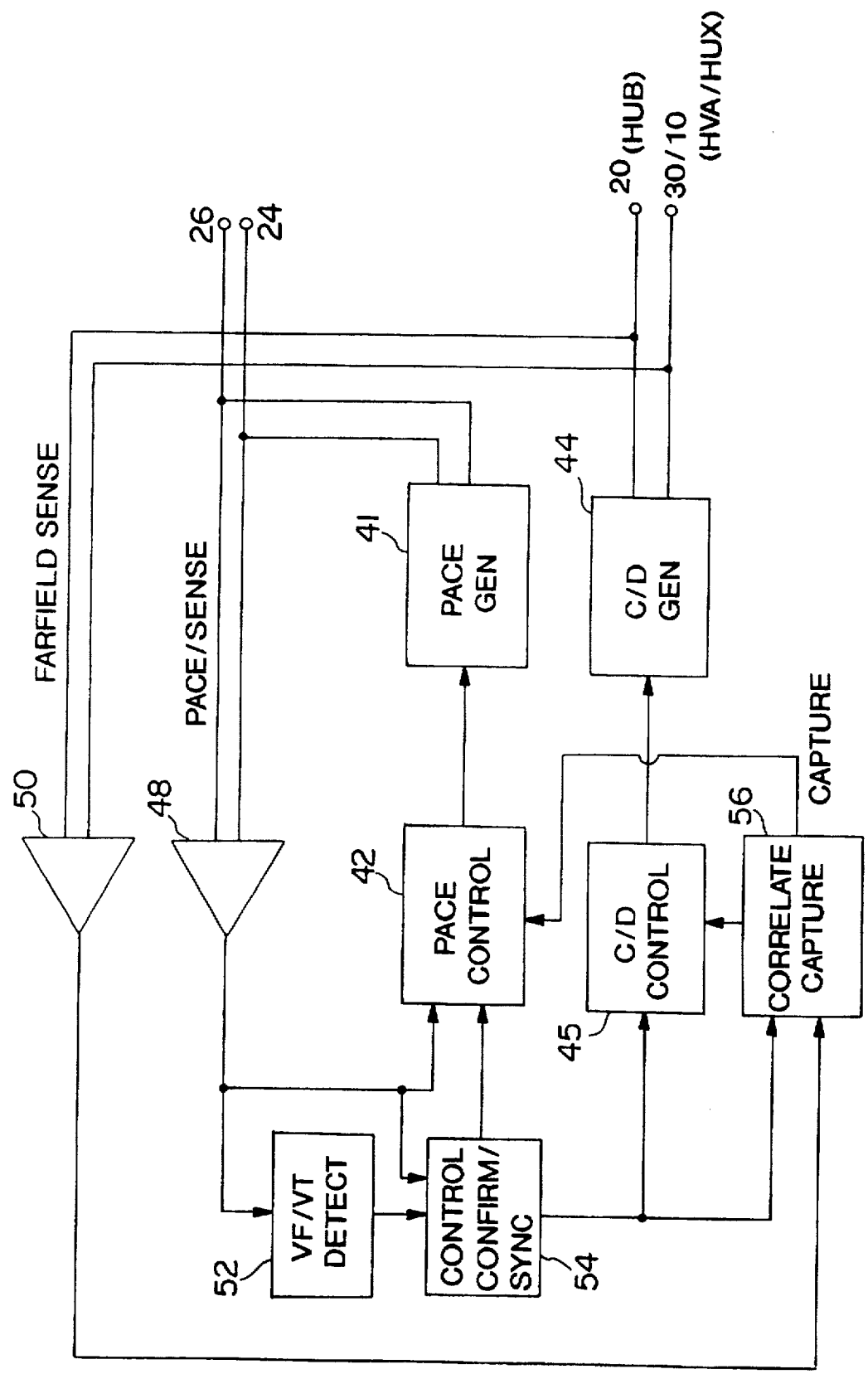
FIG. 3 is a block, functional diagram of a PCD type device adapted to carry out the confirmation and capture features of the present invention.

Referring now to FIG. 3, there is shown a block diagram illustrating the primary functional components of a PCD type apparatus in accordance with this invention. It is to be understood that the functional blocks here illustrated may be established either with hardware, software, or a combination of hardware or software, as is well known in the art. A pace generator 41, which is controlled by pace control 42, produces pacing pulses which are connected between distal electrode 26 and either electrode 30 or can 10 for unipolar pacing (not shown); or, as shown, between electrodes 26 and 24 for bipolar pacing. Electrodes 26 and 24 are also connected to the input of pace/sense amplifier/processor 48, for bipolar sensing of ventricular signals. Although not shown, bipolar sensing may also be done between electrodes 24 and 20; and unipolar sensing can be done between electrode 26 and can 10. A cardioverter/defibrillator generator 44, which is controlled by C/D control unit 45, provides an output illustrated as connected between RV coil 20 and SCV coil 30, or alternately between coil 20 and the pacemaker can 10. See referenced U.S. Pat. No. 5,188,105, for an illustration of C/D control and pulse generation. Sensed R wave signals are coupled at pace control 42, for normal control of pacing when the device is in a pacing mode. The sensed R wave signals are also connected to VF/VT detect block 52, for detection of the presence of an underlying VF/VT arrhythmia. See U.S. Pat. Nos. 5,458,619 and 5,342,402, incorporated herein by reference, which disclose generally arrhythmia detection as performed in a PCD type device. When VF/VT is detected, a signal is connected to block 54 to time out and control the confirm/sync period. This block contains the logic for carrying out the operations as set forth in the timing diagrams shown above. Thus, if the confirm/sync period times out without any R wave detection, a signal is passed to pace control 42, to cause delivery of a high level pace pulse. On the other hand, if an R wave is detected which is determined to be part of a sequence of VT or VF, a signal is sent to C/D control block 45, for causing initiation of a C/D shock by generator 44. Control confirm/sync block 54 also times out the following capture interval, and connects the timing signals to block 56. Block 56 is connected to receive a far field sense signal from block 50, which signal will be recognized at block 56 during the interval from $T_2$ to $T_3$. Block 56 suitably employs a binary correlator, which takes advantage of the binary character of signals and the fact that it can be implemented highly efficiently on a microprocessor. Such binary correlators are well known in the art.

In practice, in addition to the correlator/capture block 56 which is implemented with a microprocessor, the functions at blocks 52 and 54 are also preferably implemented with a microprocessor and appropriate software algorithm control. The remaining blocks are normally implemented by hardware, although certainly portions of these functions, such as the pace control and C/D control may be implemented by software.

Figure 4:
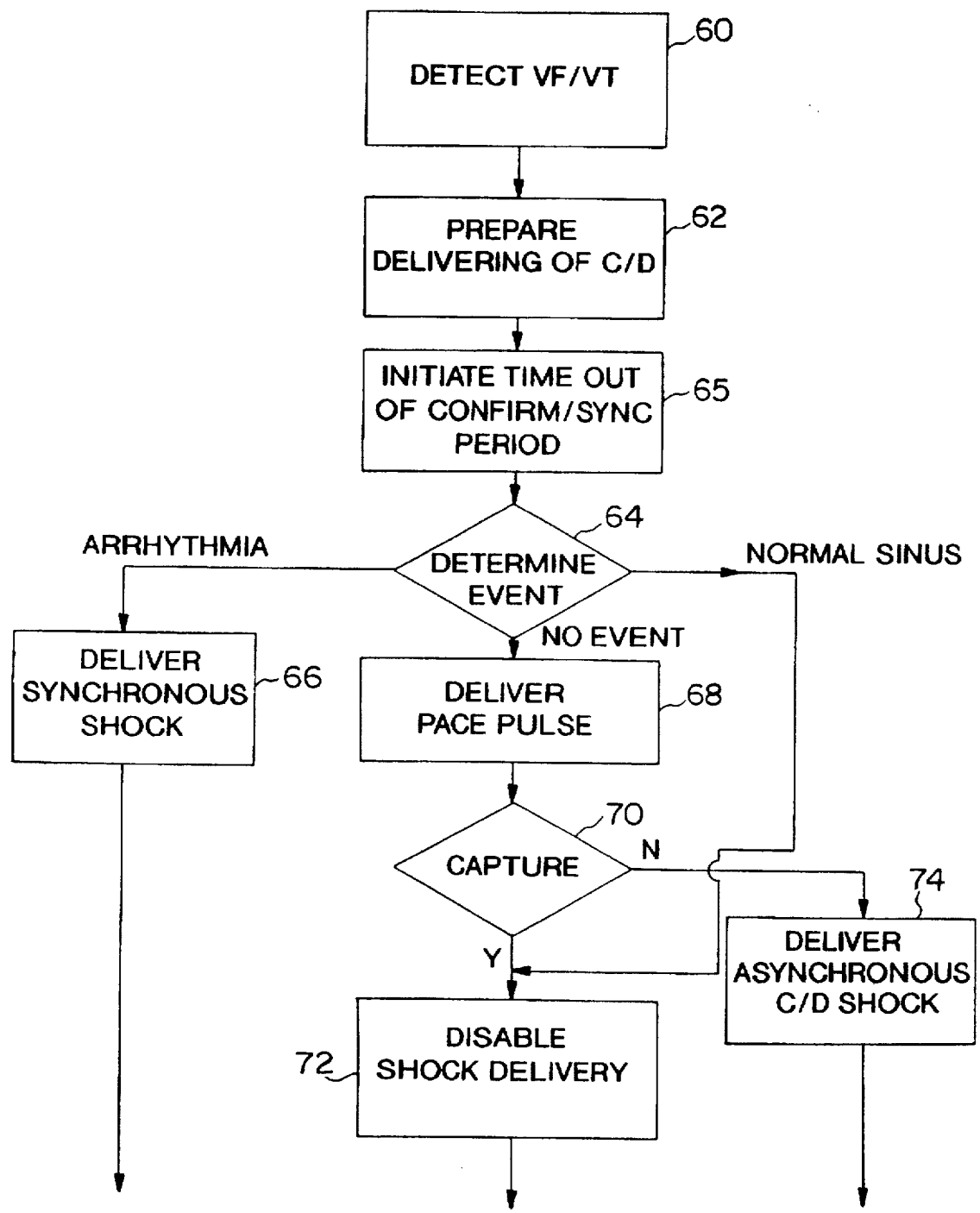
FIG. 4 is a flow diagram of the logic illustrating the method of the present invention for an episode of ventricular fibrillation.

Referring now to FIG. 4, there is shown a logic diagram for carrying out the primary functions of this invention. At 60, a determination of VF/VT is made. Following this, the PCD type unit is prepared for delivery of a C/D shock, as shown at 62. The logic then initiates time out of the confirmation/sync duration, as illustrated at 63. At 64, it is determined what, if anything, has happened during time out of the confirmation period. If arrhythmia is confirmed and a shock is indicated, the synced shock is delivered as shown at 66. If the brady escape interval has timed out, a pace pulse is delivered as illustrated at 68. At 70, it is determined whether there is an indication of capture resulting from the pace pulse, within the capture duration of around 200 ms. If yes, the shock delivery is disabled, as illustrated at 72, following which pacing may be maintained if appropriate. If no, meaning that the pace pulse did not capture the heart, this represents confirmation of the underlying arrhythmia, and the pacer applies a C/D pulse as illustrated at 74. Returning to block 64, if a normal sinus is detected, shock delivery is disabled.

There has thus been illustrated a PCD type system and method for accurately determining the presence or absence of a maintained underlying arrhythmia, i.e., distinguishing VF/VT from marked bradycardia or asystole. By using defibrillator (far field) electrodes to sense whether an R wave occurs which correlates with the delivered pace pulse, the system very accurately distinguishes a brady situation from an undersensed arrhythmia. The use of a confirm/sync period following detection of VF/VT, and limiting such period to the equivalent of a brady escape interval, enables delivery of a synchronous shock, or an asynchronous VF/VT shock when appropriate and without undue delay, while also enabling a more appropriate pacing therapy where the arrhythmia has not been maintained.

As used herein, the terms "shock," "shock pulse," and "anti-arrhythmia pulse" are used interchangeably, and refer to one or more coupled pulses delivered for defibrillation or cardioversion. The term "far field" is used as meaning sensing the R wave between two electrodes displaced from the site where the pace pulse is delivered.

What is claimed is:

1. An implantable system for detecting and treating predetermined types of cardiac fibrillation and tachycardia occurring in a patient, comprising:

sensing means for sensing cardiac signals from said patient;

detecting means for detecting an occurrence of one of ventricular fibrillation or ventricular tachycardia based on said sensed cardiac signals;

confirm means for confirming the detection of the ventricular fibrillation or ventricular tachycardia based on said sensed cardiac signals during a predetermined period following a detected fibrillation or tachycardia, said confirm means including timing means for timing out said predetermined period;

pace means for delivering a pace pulse upon the occurrence of a time out of said predetermined period without an intervening sensed cardiac signal;

capture means for determining whether said delivered pace pulse resulted in capture of the patient's heart; and shock means for delivering a shock treatment to said patient's heart when said capture means determines a lack of said capture in response to said delivered pace pulse.

2. The system as described in claim 1, wherein said sensing means further comprises far field sensing means for sensing a far field response to said delivered pace pulse, and wherein said capture means has correlation means for determining when said far field response is correlated to said delivered pace pulse.

3. The system as described in claim 2, wherein said shock means comprises shock electrode means for delivering said shock treatment, and said far field sensing means comprises means for analyzing cardiac signals sensed at said shock electrode means.

4. The system as described in claim 3, comprising a transvenous lead, said lead comprising at least one pace electrode and at least one shock electrode, said lead also having respective conductors for connecting said electrodes to said pace means and said shock means.

5. The system as described in claim 1, wherein said timing means times out said period to have a duration corresponding to a bradycardia escape interval.

6. The system as described in claim 3, comprising a transvenous lead, and wherein said shock electrode means comprises at least one coil electrode on said lead in position for placement in a patient's right ventricle.

7. A system for detecting and treating cardiac arrhythmias such as ventricular fibrillation and ventricular tachycardia when they occur in a patient, said system comprising:

a pacemaker/cardiovertor/defibrillator device, said pacemaker/cardiovertor/defibrillator device having pace means for generating and delivering pace pulses, shock means for generating anti-arrhythmia shocks, and sensing means for sensing cardiac signals from said patient;

electrode means for providing a plurality of electrodes, the electrode means coupled to the pacemaker/cardiovertor/defibrillator device one of said electrodes being a common electrode, one of said electrodes being a shock electrode for positioning within the patient's right ventricle, and one of said electrodes being a pacing electrode for positioning in proximity to the inner wall of said patient's right ventricle;

said pacemaker/cardiovertor/defibrillator device having detecting means for detecting the occurrence of an arrhythmia, timing means for timing out at least a predetermined time duration following detection of said arrhythmia, confirming means for positively confirming when said arrhythmia is maintained during the timing out of said duration, and capture means operative when there is no confirmed arrhythmia during said duration for determining if the patient's heart is not captured by a pace pulse delivered from said pace means, and shock control means for controlling said shock means to deliver said anti-arrhythmia shock when said patient's heart is not captured by a pace pulse.

8. A system for detecting and treating VF/VT forms of cardiac arrhythmia in a patient comprising, first means for determining the occurrence of a VF/VT form of arrhythmia, second means responsive to said determining of an arrhythmia for determining when said arrhythmia is maintained, said second means having (a) pace means for delivering a pace pulse to the patient's ventricle;

(b) timing means for timing out a capture interval of predetermined duration; and (c) sense means for sensing an electrical activity indicative of responsive ventricular contraction during said capture interval in response to said pace pulse, and therapy response means for delivering a shock pulse to said patient to treat said arrhythmia only when said responsive ventricular contraction is not sensed.

9. The system as described in claim 8, comprising a transvenous lead having at least one shock electrode for positioning in the patient's ventricle, at least one pacing electrode for positioning against the inner wall of said patient's ventricle, and at least a third electrode, and wherein said therapy response means is connected to deliver said shock pulse to said shock electrode and to said third electrode, and said sense means is connected to sense signals between said shock electrode and said third electrode.

10. The system as described in claim 9, wherein said shock electrode is a coil positioned on said lead so as to be placed in the patient's ventricle and said third electrode is a coil positioned on said lead so as to be placed in the patient's subclavian vein.

11. The system as described in claim 8, wherein said sense means comprises a ventricular coil electrode and a SCV electrode.

12. The system as described in claim 8 wherein the system is a pacemaker/cardiovertor/defibrillator device, said device housed in a can and a transvenous lead connected to said device, and wherein said sense means comprises a ventricular coil electrode on said lead and a common electrode positioned on said can.

13. The system as described in claim 8, wherein said pace means comprises a pace electrode for delivering pace pulses to a pacing site on the inner wall of said patient's ventricle, and said sense means comprises a pair of electrodes displaced from said pacing site.

14. The system as described in claim 8, wherein said second means further comprises confirm means operative before delivery of a pace pulse, for confirming when said VF/VT arrhythmia is maintained and for controlling said therapy response means to deliver said shock pulse whenever said VF/VT arrhythmia is confirmed.

15. A method of determining when an anti-arrhythmia pulse can be safely delivered, the method comprising the steps of:

detecting the occurrence of a VF/VT arrhythmia;

timing out a limited time interval following said detection;

determining during said limited time interval following said detection, if said arrhythmia is maintained and delivering an anti-arrhythmia shock to said patient in response to a determined maintained arrhythmia;

when an arrhythmia is not determined to be maintained during said limited time period, delivering a pace pulse to said patient's ventricle, and determining whether said patient's ventricle is captured by said pace pulse; and following a delivered pace pulse, delivering an anti-arrhythmia shock only when said ventricle is not determined to have been captured.

16. The method of claim 15, wherein said capture determination comprises sensing for a far field R wave signal.

17. The method of claim 16, wherein said capture determination comprises sensing for a far field R wave during a predetermined interval following delivering a pace pulse, and correlating a sensed far field R wave with said pace pulse.

18. The method of claim 15, comprising delivering said pace pulse immediately upon the end of said limited time interval.

19. The method of claim 15, wherein the step of timing out said limited time interval comprises timing out said limited time interval corresponding to a rate within the range of 60–120 bpm.

20. The method of claim 15, comprising determining when a normal sinus beat occurs within said limited time interval, and disabling delivery of said shock when said normal sinus beat is determined.

* * * * *